US011980394B2

(12) United States Patent
Bateman et al.

(10) Patent No.: US 11,980,394 B2
(45) Date of Patent: May 14, 2024

(54) DEVICE FOR REMOVAL OF IMPLANTS AND ASSOCIATED METHOD OF USE

(71) Applicant: Bateman Bottle, LLC, Wilmington, DE (US)

(72) Inventors: Michael Bateman, Highland Ranch, CO (US); Andy Edward Denison, Temecula, CA (US); Peter John D'Aquanni, Murrieta, CA (US)

(73) Assignee: Bateman Bottle, LLC, Wilmington, DE (US)

( * ) Notice: Subject to any disclaimer, the term of this patent is extended or adjusted under 35 U.S.C. 154(b) by 755 days.

(21) Appl. No.: 16/645,767

(22) PCT Filed: Jun. 5, 2018

(86) PCT No.: PCT/US2018/036106
§ 371 (c)(1),
(2) Date: Mar. 9, 2020

(87) PCT Pub. No.: WO2018/226726
PCT Pub. Date: Dec. 13, 2018

(65) Prior Publication Data
US 2020/0281626 A1      Sep. 10, 2020

Related U.S. Application Data

(60) Provisional application No. 62/515,314, filed on Jun. 5, 2017.

(51) Int. Cl.
*A61B 17/34*      (2006.01)
*A61B 17/00*      (2006.01)

(52) U.S. Cl.
CPC ............... *A61B 17/3468* (2013.01); *A61B 2017/00455* (2013.01); *A61B 2017/00792* (2013.01);
(Continued)

(58) Field of Classification Search
CPC .......... A61B 17/3468; A61B 2217/005; A61B 2017/00796; A61B 2017/00792;
(Continued)

(56) References Cited

U.S. PATENT DOCUMENTS 3,661,144 A    5/1972  Jensen et al.
4,135,515 A    1/1979  Muriot
(Continued)

FOREIGN PATENT DOCUMENTS

CN    202892006 U    4/2013
DE     3033234 C2    3/1982
(Continued)

OTHER PUBLICATIONS

J.K. O'Neill, G.I. Taylor, A novel method to remove silicone gel after breast implant rupture, Journal of Plastic, Reconstructive & Aesthetic Surgery, vol. 59, Issue 8, 2006, pp. 889-891 (Year: 2006).*

(Continued)

*Primary Examiner* — Sarah A Long
*Assistant Examiner* — Raihan R Khandker
(74) *Attorney, Agent, or Firm* — Johnston IP Law, PLLC (57) ABSTRACT

An implant removal device for removal of ruptured silicone breast implants includes a hollow container having a middle portion disposed between a first end and a second end. The device also has a connector port coupled to the second end that is coupled to a suction device during use. The device also includes a nozzle coupled to the first end that is configured for placement against an incision of a patient for removing a ruptured breast implant from the patient. The positioning of the nozzle on said first end is offset from a longitudinal axis that extends in a direction parallel to the length of the middle portion and within the middle portion.

(Continued)

The nozzle opening may include gripping portions for aiding in gripping the implant shell during the removal process.

13 Claims, 7 Drawing Sheets

(52) U.S. Cl.
CPC ............ A61B 2017/00796 (2013.01); A61B 2217/005 (2013.01)

(58) Field of Classification Search
CPC .. A61F 2/12; A61M 1/60; A61M 1/00; A61M 1/81; A61M 1/815
See application file for complete search history.

(56) References Cited

U.S. PATENT DOCUMENTS

| | | | |
|---|---|---|---|
| 4,465,485 A | 8/1984 | Kashmer et al. | |
| 4,643,733 A | 2/1987 | Becker | |
| 4,908,011 A | 3/1990 | Jacobsen et al. | |
| 4,915,691 A | 4/1990 | Jones et al. | |
| 5,242,434 A | 9/1993 | Terry | |
| 5,295,957 A | 3/1994 | Aida et al. | |
| 5,391,203 A | 2/1995 | Bartlett et al. | |
| 5,411,475 A | 5/1995 | Atala et al. | |
| D359,118 S | 6/1995 | Nates | |
| 5,533,516 A | 7/1996 | Sahatjian | |
| 5,658,328 A | 8/1997 | Johnson et al. | |
| 5,720,299 A | 2/1998 | Theodoru et al. | |
| 5,776,119 A | 7/1998 | Bilbo et al. | |
| D409,303 S | 5/1999 | Oepping | |
| 6,106,455 A | 8/2000 | Kan | |
| 6,299,033 B1 | 10/2001 | VerWeyst et al. | |
| D460,551 S | 7/2002 | Swenson | |
| 6,419,699 B1 | 7/2002 | Schuessler | |
| 6,485,452 B1 | 11/2002 | French et al. | |
| 6,503,264 B1 | 1/2003 | Birk | |
| 6,589,219 B1* | 7/2003 | Shibuya ............... A61G 7/0503 604/319 |
| 6,632,182 B1 | 10/2003 | Treat | |
| 7,029,454 B2 | 4/2006 | Watanabe | |
| D583,929 S | 12/2008 | Reusch | |
| 7,727,226 B2 | 6/2010 | Chang et al. | |
| 7,744,527 B2 | 6/2010 | Cohn | |
| D630,728 S | 1/2011 | Dombrowski et al. | |
| 8,088,101 B2 | 1/2012 | Chang et al. | |
| D680,640 S | 4/2013 | Merchant et al. | |
| 8,454,690 B2 | 6/2013 | McClellan | |
| 8,591,496 B2 | 11/2013 | Caruso et al. | |
| 8,721,520 B2 | 5/2014 | Caira et al. | |
| 8,784,486 B2 | 7/2014 | Schuessler | |
| 8,961,392 B2 | 2/2015 | Cao et al. | |
| 9,044,209 B2 | 6/2015 | Dayton et al. | |
| 9,044,547 B2 | 6/2015 | Tremolada | |
| 9,119,926 B2 | 9/2015 | Cuevas et al. | |
| D741,992 S | 10/2015 | Roeper | |
| 9,215,964 B2 | 12/2015 | Loske | |
| 9,295,764 B2 | 3/2016 | Christensen et al. | |
| 9,327,091 B2 | 5/2016 | Wang et al. | |
| 9,427,295 B2 | 8/2016 | Connors et al. | |
| 9,615,911 B2 | 4/2017 | Connors et al. | |
| 9,636,090 B2 | 5/2017 | Li | |
| 9,681,941 B2 | 6/2017 | Griffin et al. | |
| 9,750,856 B2 | 9/2017 | Baker et al. | |
| D819,803 S | 6/2018 | Kheradpir et al. | |
| D820,972 S | 6/2018 | Klever et al. | |
| D821,567 S | 6/2018 | Feldman et al. | |
| 10,478,587 B2 | 11/2019 | Tremolada | |
| 11,485,552 B2 | 11/2022 | Armstrong et al. | |
| 2002/0082569 A1 | 6/2002 | Wildman | |
| 2003/0195482 A1 | 10/2003 | Schultz | |
| 2005/0149186 A1 | 7/2005 | Roballey et al. | |
| 2006/0155211 A1 | 7/2006 | McQuaid | |
| 2006/0167469 A1 | 7/2006 | Arden | |
| 2008/0009891 A1 | 1/2008 | Cohn | |
| 2009/0005747 A1 | 1/2009 | Michaels et al. | |
| 2009/0099636 A1 | 4/2009 | Chanduszko et al. | |
| 2009/0177165 A1 | 7/2009 | Tsao | |
| 2009/0187195 A1 | 7/2009 | Berk et al. | |
| 2010/0125171 A1 | 5/2010 | Kelner | |
| 2010/0228188 A1 | 9/2010 | Kunzler et al. | |
| 2011/0190804 A1 | 8/2011 | Sekino et al. | |
| 2011/0237920 A1 | 9/2011 | Glaser et al. | |
| 2012/0004629 A1 | 1/2012 | Asfora | |
| 2012/0238972 A1 | 9/2012 | Karpowicz et al. | |
| 2013/0211440 A1 | 8/2013 | Schwab et al. | |
| 2013/0226114 A1 | 8/2013 | Massi et al. | |
| 2013/0325120 A1 | 12/2013 | McClellan | |
| 2014/0005641 A1 | 1/2014 | Slade et al. | |
| 2014/0222145 A1 | 8/2014 | Kronowitz | |
| 2014/0316302 A1 | 10/2014 | Nonnemacher et al. | |
| 2014/0323914 A1 | 10/2014 | VanderWoude et al. | |
| 2014/0378342 A1 | 12/2014 | Baker et al. | |
| 2015/0148588 A1 | 5/2015 | Connors et al. | |
| 2015/0182256 A1* | 7/2015 | Berk ............... A61B 17/22031 606/127 |
| 2015/0258257 A1 | 9/2015 | Kidman et al. | |
| 2015/0314050 A1 | 11/2015 | Beer | |
| 2015/0374478 A1 | 12/2015 | Anderson | |
| 2016/0228603 A1 | 8/2016 | Nguyen et al. | |
| 2016/0250017 A1 | 9/2016 | McClellan | |
| 2016/0256650 A1 | 9/2016 | Wang et al. | |
| 2016/0279305 A1 | 9/2016 | Esnouf et al. | |
| 2016/0325063 A1 | 11/2016 | Khosrowshahi et al. | |
| 2017/0095600 A1 | 4/2017 | Sherman et al. | |
| 2017/0112977 A1 | 4/2017 | Thompson et al. | |
| 2017/0136209 A1 | 5/2017 | Burnett et al. | |
| 2017/0172726 A1 | 6/2017 | Beeckler | |
| 2017/0245980 A1 | 8/2017 | Govari et al. | |
| 2017/0266396 A1 | 9/2017 | Feldman et al. | |
| 2019/0125401 A1* | 5/2019 | Chacon Quiros .. A61B 17/3468 |

FOREIGN PATENT DOCUMENTS

| | | |
|---|---|---|
| DE | 3033234 C2 | 3/1985 |
| DE | 3740851 A | 6/1988 |
| DE | 3740851 A1 | 6/1988 |
| DE | 19603198 A1 | 7/1997 |
| EP | 1234589 A1 | 8/2002 |
| EP | 1765432 B1 | 4/2013 |
| EP | 3087951 A1 | 11/2016 |
| EP | 2384776 B1 | 5/2017 |
| FR | 2564321 A1 | 11/1985 |
| GB | 1197910 A | 7/1970 |
| GB | 2198358 B | 7/1991 |
| GB | 9006851242-0001 | 9/2019 |
| JP | 5960689 B2 | 8/2016 |
| JP | 6108279 B2 | 4/2017 |
| KR | 101392731 B1 | 5/2014 |
| KR | 20150111228 A | 10/2015 |
| KR | 300879370.0000 | 11/2016 |
| WO | 02049692 A2 | 6/2002 |
| WO | 2005120599 A1 | 12/2005 |
| WO | WO 2005120599 A1 | 12/2005 |
| WO | 2009023766 A1 | 2/2009 |
| WO | 2011087788 A2 | 7/2011 |
| WO | 2011140382 A1 | 11/2011 |
| WO | 2011145075 A2 | 11/2011 |
| WO | 2012141964 A2 | 10/2012 |
| WO | 2013166484 A1 | 11/2013 |
| WO | 2014066337 A2 | 5/2014 |
| WO | 2014089028 A1 | 6/2014 |
| WO | 2016109394 A1 | 7/2016 |
| WO | 2017023674 A1 | 2/2017 |
| WO | 2017087182 A1 | 5/2017 |
| WO | 2017141278 A1 | 8/2017 |
| WO | 2017181144 A2 | 10/2017 |

OTHER PUBLICATIONS

English language description for KR 300879370.0000 extracted from espacenet.com database on May 25, 2023, 1 page.

(56) References Cited

OTHER PUBLICATIONS

Youtube, "Medi-Vac Fluid Managemnt Products Video", Cardinal Health, https://www.youtube.com/watch?v=DCz970B68a4, Oct. 9, 2014, 1 page.
Youtube, "SAC-NPS-2000 Negative Pressure Wound Therapy Instrument Video", https://www.youtube.com/watch?v=5DO1rVU5G38, Jun. 15, 2021, 1 page.
International Search Report for Application No. PCT/US2018/036106 dated Oct. 26, 2018, 1 page.
Tuttle, Todd. M. et al., "Postmastectomy Reconstruction Outcomes After Intraoperative Evaluation With IndoCyanine Green Aniography Versus Clinical Assessment", Annals of Surgical Oncology, vol. 23, 2016, pp. 4080-4085.
Design U.S. Appl. No. 29/685,427, filed Mar. 28, 2019, 7 pages.
English language abstract for CN 202892006 U extracted from espacenet.com database on May 18, 2020, 1 page.
English language abstract for DE 3033234 C2 extracted from espacenet.com database on May 18, 2020, 1 page.
English language abstract for DE 3740851 A extracted from espacenet.com database on May 18, 2020, 1 page.
English language abstract for DE 19603198 A1 extracted from espacenet.com database on May 18, 2020, 1 page.
English language abstract for EP 1765432 B1 extracted from espacenet.com database on May 18, 2020, 1 page.
English language abstract for FR 2564321 A1 extracted from espacenet.com database on May 18, 2020, 1 page.
English language abstract for JP 5960689 B2 extracted from espacenet.com database on May 18, 2020, 2 pages.
English language abstract for JP 6108279 B2 extracted from espacenet.com database on May 18, 2020, 1 page.
English language abstract for KR 101392731 B1 extracted from espacenet.com database on May 18, 2020, 1 page.
English language abstract for KR 20150111228 A extracted from espacenet.com database on May 18, 2020, 1 page.
English language abstract for WO 2005120599 A1 extracted from espacenet.com database on May 18, 2020, 1 page.

* cited by examiner

DEVICE FOR REMOVAL OF IMPLANTS AND ASSOCIATED METHOD OF USE

CROSS REFERENCE TO RELATED APPLICATIONS

The present invention is the National Stage of International Patent Application No. PCT/US2018/036106, filed on Jun. 5, 2018, which claims priority to U.S. Provisional Patent Application No. 62/515,314, filed on Jun. 5, 2017, the disclosure of which is herein incorporated by reference.

FIELD OF THE DISCLOSURE

The present invention relates, generally, to a device used to remove implants from a patient, and typically silicone breast implants.

DESCRIPTION OF THE RELATED ART

A breast implant is a prosthesis used to change the size, shape, and contour of a human breast. Breast implants are implanted under the breast tissue or under the chest muscle to increase breast size (augmentation), to rebuild breast tissue after mastectomy or other damage to the breast (reconstruction), or to correct congenital defects in the chest wall. They are also used in revision surgeries, which correct or improve the result of an original surgery.

Breast implants are available in many different forms. There are two types of breast implants approved for sale in the United States: saline-filled breast implants (i.e., saline breast implants), in which an implant shell is filled with sterile salt water, and silicone-filled breast implants (i.e., silicone breast implants), in which the implant shell is filled with a silicone gel. Both types have a silicone outer shell. They vary in size, shell thickness, shell surface texture, and shape (contour).

Ruptured silicone breast implants can result after placement into the human body. A rupture is a tear or hole in the outer shell of the breast implant. When this occurs in a saline breast implant, it deflates, meaning the saltwater (saline) solution leaks from the shell. Silicone gel is thicker than saline, so when a silicone gel-filled implant ruptures, the gel may remain in the shell or in the scar tissue that forms around the implant (intracapsular rupture). Silicone gel that leaks outside the capsule surrounding the implant may travel (migrate) away from the breast. The leaked silicone gel may cause lumps to form in the breast or in other tissue, most often the chest wall, armpit or arm. It may be difficult or impossible to remove silicone gel that has traveled to other parts of the body. Ruptured silicone breast implants can cause breast pain or changes in the contour or shape of the breast. Accordingly, the FDA (Food and Drug Administration of the United States) recommends removing both saline-filled and silicone gel-filled breast implants if they have ruptured.

In many instances, it is desirable to remove the ruptured silicone breast implant and the leaking silicone gel. Removal after rupture is a time consuming, tedious and difficult process. Typically, such removal is performed by manual extraction utilizing surgical sponges.

The present disclosure provides a simple, efficient device and associated method to address this problem. The device of the present disclosure is also appropriate for the removal of other types of implants from a patient, including un-ruptured silicone breast implants, saline breast implants, and buttocks implants and the like that include an outer shell that is filled with saline or silicone gel or another filling material.

SUMMARY OF THE INVENTION

The present disclosure is directed to an implant removal device, and a system including the implant removal device, and an associated method for removing an implant using the device and system.

The implant removal device comprises a hollow container extending between a first end and a second end along a longitudinal axis with a middle portion disposed between the first and second end for receiving and containing the implant. The hollow container has an interior container surface defining a volume therewithin. A connector port is coupled to the second end of the hollow container and is adapted for connection to the suction device. A nozzle is coupled to the first end of said hollow container and extends away from the first end along a nozzle axis and terminates at a nozzle opening defining a terminal end surface.

In certain embodiments, the nozzle opening includes at least one gripping portion and at least one recessed portion. The one or more gripping portions preferably are brought into contact with the shell of the implant when the device is inserted into the patient and aid in gripping or maintaining the shell in place during the removal process. In other embodiments, the nozzle axis is offset from the longitudinal axis such that the nozzle opening is offset from the middle portion of the hollow container for aligning with the implant during the removal process. In still further embodiments the device includes both sets of features.

To remove an implant from a patient, the implant removal device is coupled to a suction device and the device is inserted within an incision in the patient such that the nozzle is brought into proximity to the implant. The suction device is then actuated to create negative pressure in the volume of the hollow container through the connector port sufficient to draw out the shell and, in the case of silicone-filled implants, the silicone gel from the patient through the nozzle opening and into the volume of the hollow container.

BRIEF DESCRIPTION OF THE DRAWINGS

Other advantages of the present invention will be readily appreciated, as the same becomes better understood by reference to the following detailed description when considered in connection with the accompanying drawings.

DETAILED DESCRIPTION OF THE INVENTION

Figure 6:
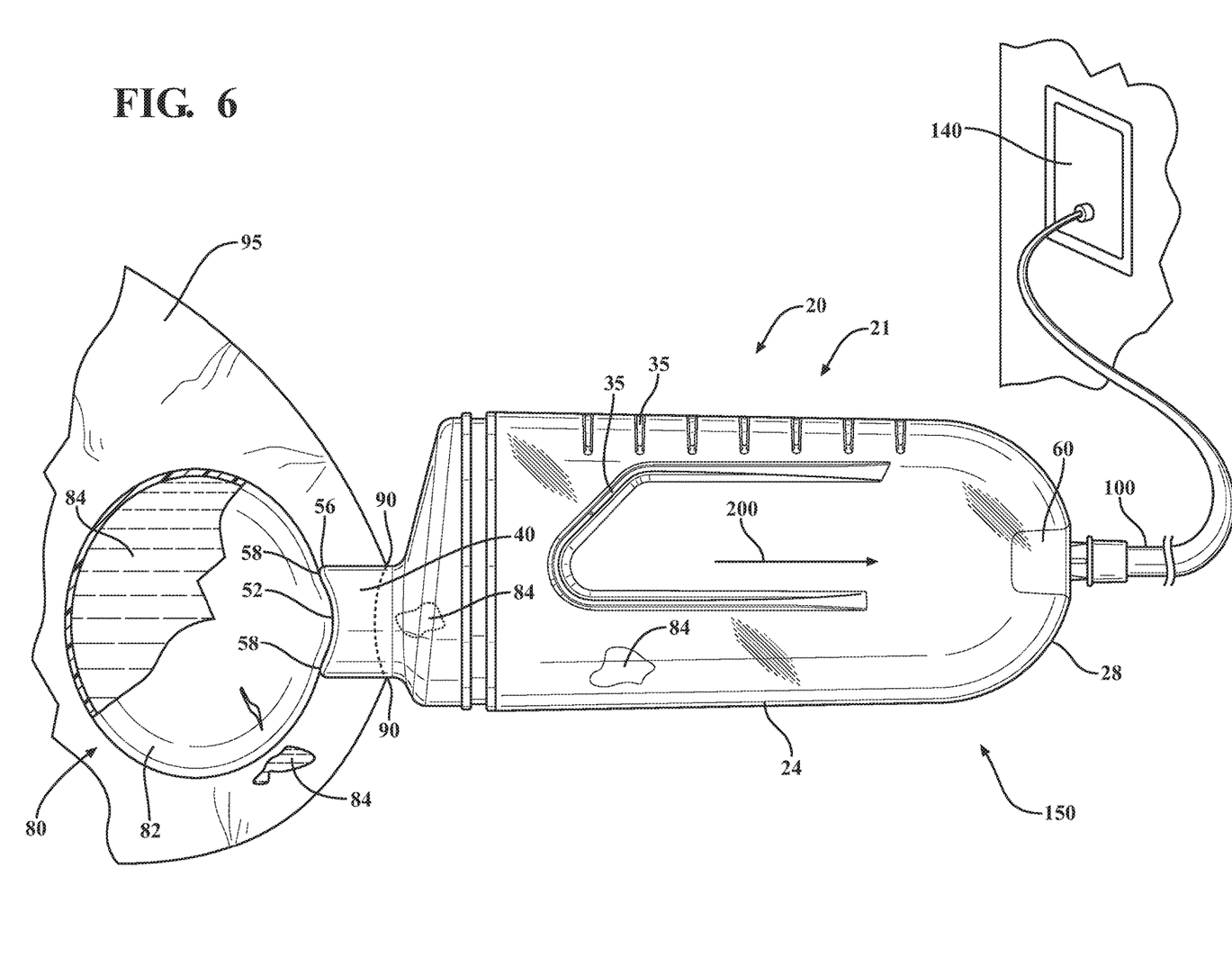
FIG. 6 is a partial section view of the use of the implant removal system of FIG. 5 in removing an implant from a patient in an operating room.
Figure 7:
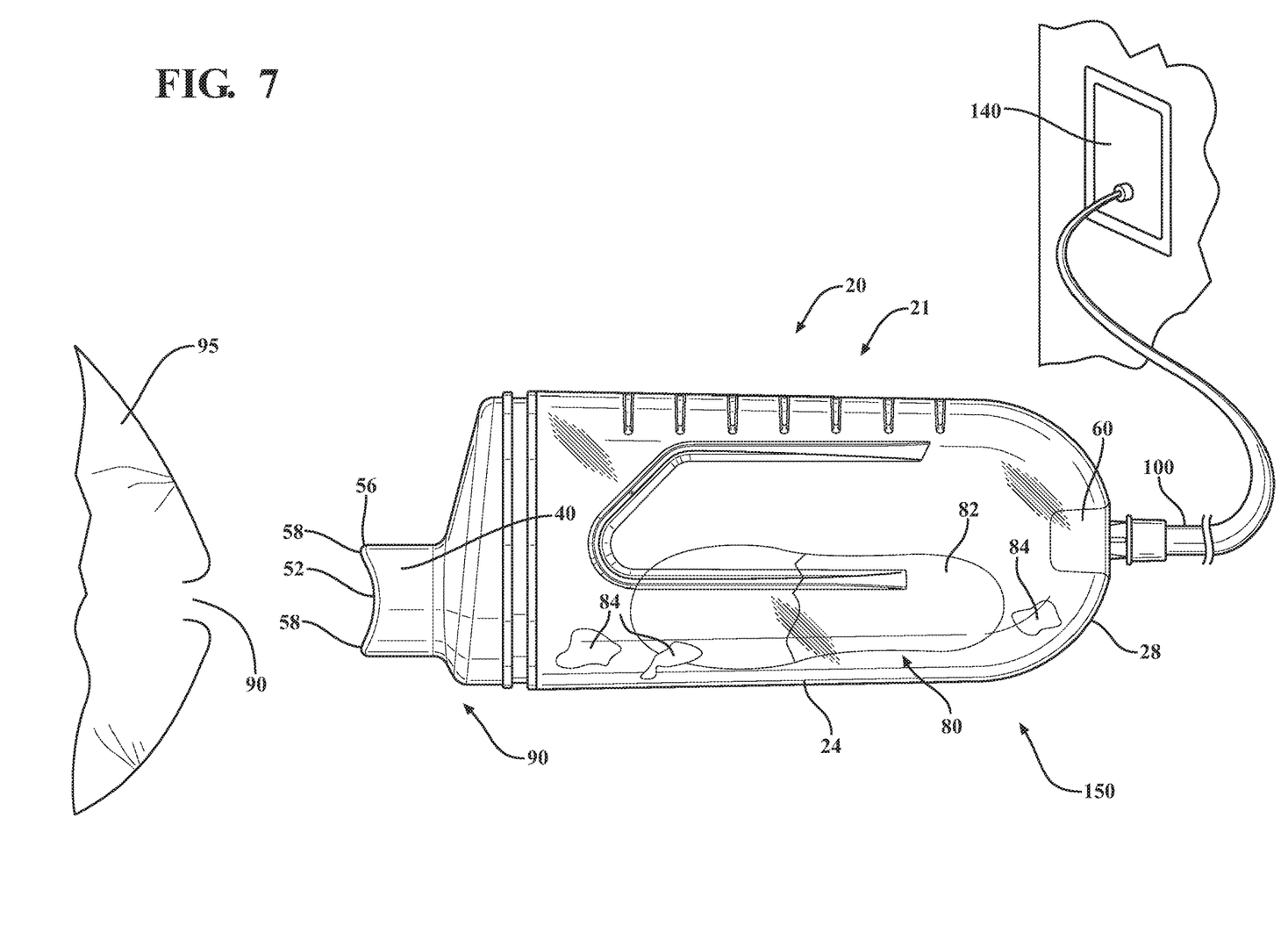
FIG. 7 is a partial section view of the implant removal system after removal of an implant in which the shell and gel of the implant is contained within the hollow container.

With reference to the Figures, an implant removal device 21 for use in an implant removal system 20 is disclosed herein that is configured for the removal of an implant, and in particular silicone gel-filled implants, from a patient during a surgical procedure. The disclosure also describes the use of the implant removal device 21 for removing an implant (shown as 80 in FIGS. 6 and 7 below), and in particular a silicone gel filled implant such as a breast implant, but could also be used in the removal of other implants that include a shell (shown as 82 in FIGS. 6 and 7 below) and a gel or other filling material (shown as silicone gel 84 in FIGS. 6 and 7 below), such as a saline-filled implant, a buttocks implant, or the like. For ease of description, the description of the shell 82 and the gel 84 as used hereinafter, refers to any type of implant 80 that includes such components, including but not limited to silicone-filled implants 80 such as illustrated in FIGS. 6 and 7.

Referring first to FIGS. 1-5, the implant removal device 21 disclosed herein is in the form of a hollow container 22 having a middle portion 24 disposed between a first end 26 and a second end 28. In certain embodiments, the hollow container 22 is generally bottle-shaped, with the middle portion 24 being substantially circular or oval-shaped in cross-section. However, in other embodiments, the hollow container 22 may be shaped different. By way of example, as opposed to being substantially circular or oval-shaped in cross-section, the middle section 24 may be rectangular or triangular in cross-section, with the respective shapes of the first end 26 and second end 28 modified so as to correspond to the shape of the modified middle portion 24.

The middle portion 24, first end 26, and the second end 28 collectively have an interior container surface 30, which further defines a volume 32, and an exterior container surface 34 opposite the interior container surface 30. The distance between the interior container surface 30 and the exterior container surface 34 defines a thickness of the hollow container 22 corresponding to the middle portion 24, first end 26, or the second end 28. The volume 32 of the hollow container 22 should be sufficient to contain the entirety of the implant shell and silicone gel of the implant (respectively identified by reference numerals 82, 84 and 80 in FIG. 6) removed during the surgical procedure. For example, in certain embodiments, the volume 32 may be between 100 and 5000 cubic centimeters, such as 1000 cubic centimeters, although in further embodiments smaller and larger volumes are contemplated.

In the embodiments illustrated, a longitudinal axis 25 may also be defined within the volume 32 that extends generally parallel to the length L1 of the middle portion 24 in a direction from the first end 26 to the second end 28. In embodiments wherein the middle portion 24 is symmetrical in cross-section, the longitudinal axis 25 may further defined as extending on a line that is equidistant from the interior container surface 30 of the middle portion 24.

To aid in gripping the exterior container surface 34 of the device 21, a series of one or more protrusions or recesses (shown here as protrusions 35) may be included on the exterior container surface 34 of the hollow container 22, such as on one or more protrusions 35 or recesses on the exterior container surface 34 of the middle portion 24, the first end 26, and/or the second end 28 (shown in FIGS. 1A, 1B, 2, 6 and 7) as being included on the middle portion 24).

A nozzle 40 is coupled to the first end 26 of the hollow container 22 which extends transversely in a direction away from the first end 26 and the second end 28. The nozzle 40 is configured for interfacing with the implant 80 through the surgical incision 90 (see FIG. 6) of a patient 95 during the surgical procedure to remove the implant 80. In certain embodiments, the positioning of the nozzle 40 is offset from the longitudinal axis 25, as will be described further below.

The nozzle 40 includes an interior nozzle surface 44 that extends outwardly from, or otherwise transitions outwardly from, the interior container surface 34 of the first end 26. In addition, the nozzle 40 includes an exterior nozzle surface 46 that extends outwardly from, or otherwise transitions outwardly away from, the exterior container surface 34 of the first end 26.

The interior container surface 44 of the nozzle 40 extends away from the first end 26 and terminates at a nozzle opening 50. The nozzle opening 50 functions as the inlet port for the receipt of the ruptured breast implant shell 82 and silicone gel 84 to the volume 32 of the hollow container 22 during the surgical procedure. The nozzle opening 50 is open to the volume 32 of the hollow container 22. The size of the nozzle opening 50 may vary depending upon the ultimate end use of the implant removal device 21. In particular, the size of the nozzle opening 50 may be enlarged or diminished in cases where larger amounts of material, including the ruptured breast implant 80, shell 82, or gel 84, is desired to be removed from the patient 95.

As noted above, in certain embodiments, the nozzle 40 is coupled to the first end 26 such that it is offset relative to the longitudinal axis 25. In particular, the nozzle 40 defines a nozzle axis 27 extending in a direction away from the first end 26, and preferably away and transverse to the first end 26, and in a direction that is parallel to, and radially spaced from, the longitudinal axis 25. With this configuration, the nozzle 40 is more easily positioned such that it may be located in closer proximity to the incision 90 along the skin of the patient 95 when the device 21 is used to remove the implant 80 during the implant removal process as compared with a nozzle 40 aligned along the longitudinal axis 25.

In certain embodiments, in addition to the nozzle opening 50 being offset from the longitudinal axis, the nozzle 40 is spaced from an exterior container surface 34 of the middle portion 24 toward said longitudinal axis 25.

In certain embodiments, the nozzle opening 50 includes at least one recessed portion 52 and at least one gripping portion 56. In further embodiments, the nozzle opening 50 includes a plurality of recessed portions 52 and a plurality of gripping portion 56, with each of the gripping portions 56 separated from each other by one of the respective pair of recessed portions 52, and vice versa. In the embodiments shown in FIGS. 1-7, the nozzle opening 50 includes a pair of recessed portions 52 and a pair of gripping portions 56, with each of the pair of gripping portions 56 separated from each other by one of the respective pair of recessed portions 52.

In certain embodiments, the gripping portions 56 define a terminal end surface 48 having an apex 58, with the apex 58 of each of the gripping portions 56 spaced further away from the first end 26 than the recessed portions 52.

Further, in certain embodiments, each of the recessed portions 52 are curved the gripping portions 56 so as to define a curved end surface 57. In these embodiments, the recessed portions 52 have a vertex 54 between a respective apexes 58 of the gripping portions 56. The distance between the apex 58 of the gripping portions 56 and the vertex 54 of the recessed portions 52 define a depth D1 of the recessed portions 52.

When the implant removal device 20 is used to remove the implant 80, as will be described in further detail below with respect to the removal of a ruptured breast implant as illustrated in FIG. 6, the terminal end surface 48 corresponding to the apex 58 of each of the gripping portions 56 is brought into proximity with, and preferably brought into contact with, the shell 82 of the implant 80, and functions to aid in holding or otherwise gripping the shell 82 of the implant 80 during the removal process. In order to aid in this function, it is preferable that the nozzle 40, and in particular the gripping portions 56 of the nozzle opening 50, is formed from a material and has dimension to have sufficient rigidity that they resist deformation when contacting the shell 82 (i.e., the curved gripping portions 56 in particular and the nozzle 40 in general do not bend or collapse when contacting the shell 82), and in particular being pressed against the shell 82, during the process of removing the implant 80. Further, the nozzle 40 and nozzle opening 50 also resist deformation while contacting the shell 82 as described above while negative pressure is applied to the device 21 during the process of removing the implant 80.

It has been surprisingly and unexpectedly discovered that this offset positioning of the nozzle 40 relative to the longitudinal axis 25 and along the nozzle axis 27, in combination with the rigidity of the nozzle 40, and particularly in combination with the inclusion of one or more gripping portions 56 on the nozzle 40, provides a maximum efficiency in the removal of the implant shell 82 and silicone gel 84 of the implant 80 during the removal process, as will be described in further detail below.

In certain embodiments, such as shown in the Figures herein, the first end 26 and the nozzle 40 are a one-piece structure, with the one-piece structure being is coupled to, or otherwise secured to, the distinct middle portion 24 to form the hollow container 22 prior to use. Stated another way, the nozzle 40 is integrally formed with the first end 26 as a one-piece structure which is distinct from the structure of the middle portion 24 and second end 28.

In certain embodiments, the hollow container 22 includes a first cap 29 defining the first end 26, with an outer peripheral end 42 of the first cap 29 being coupled to the middle portion 24. In particular, the outer peripheral end 42 of the first cap 29 is positioned adjacent to, or is otherwise coupled or sealed to, a terminal end region 31 of the middle portion 24. In embodiments described below, the first cap 29 is shown as being press fit and/or ultrasonically welded to the middle portion 24.

Figure 1A:
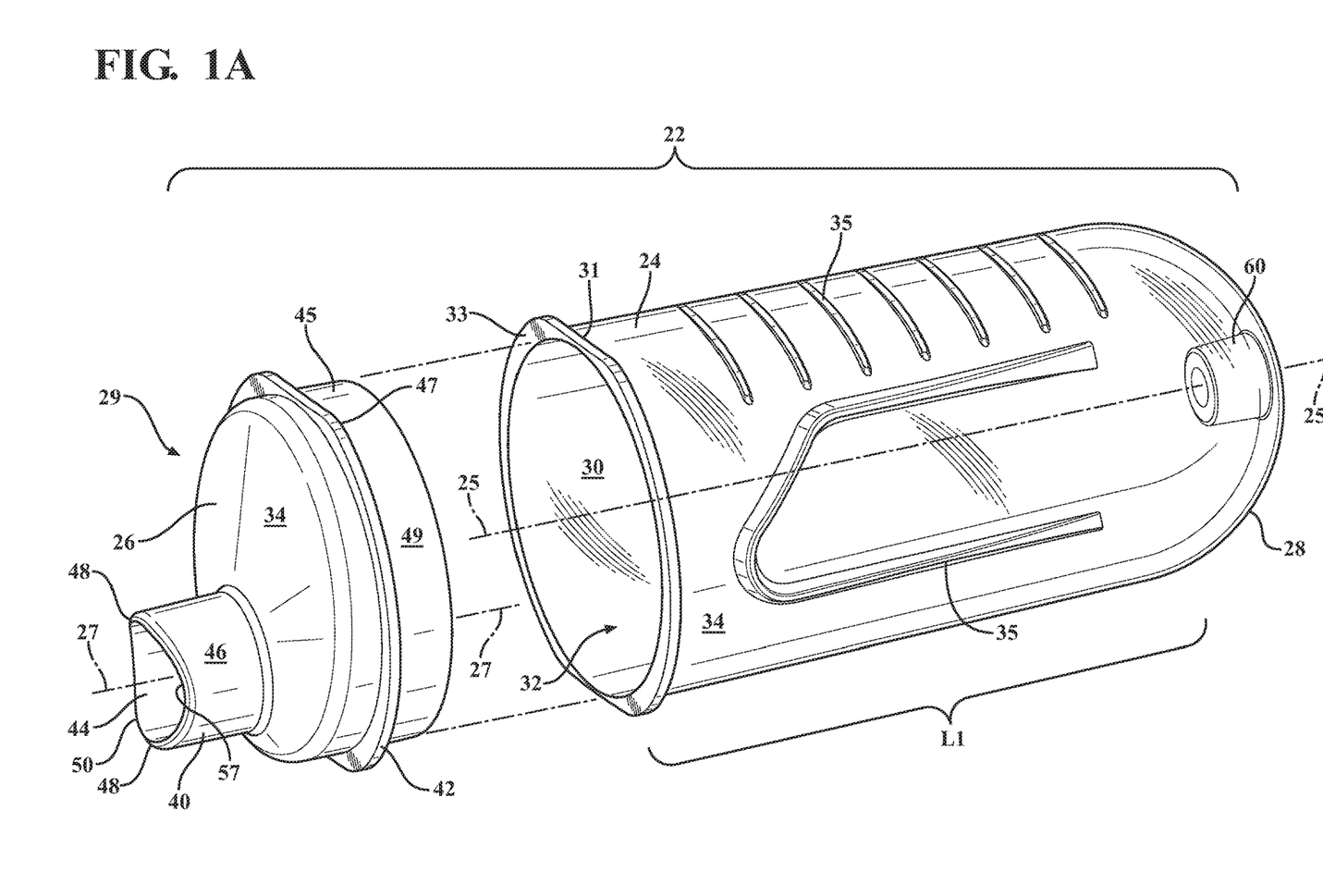
FIG. 1A is a perspective view of the first end of the implant removal device according to one exemplary embodiment.
Figures 4, 4A:
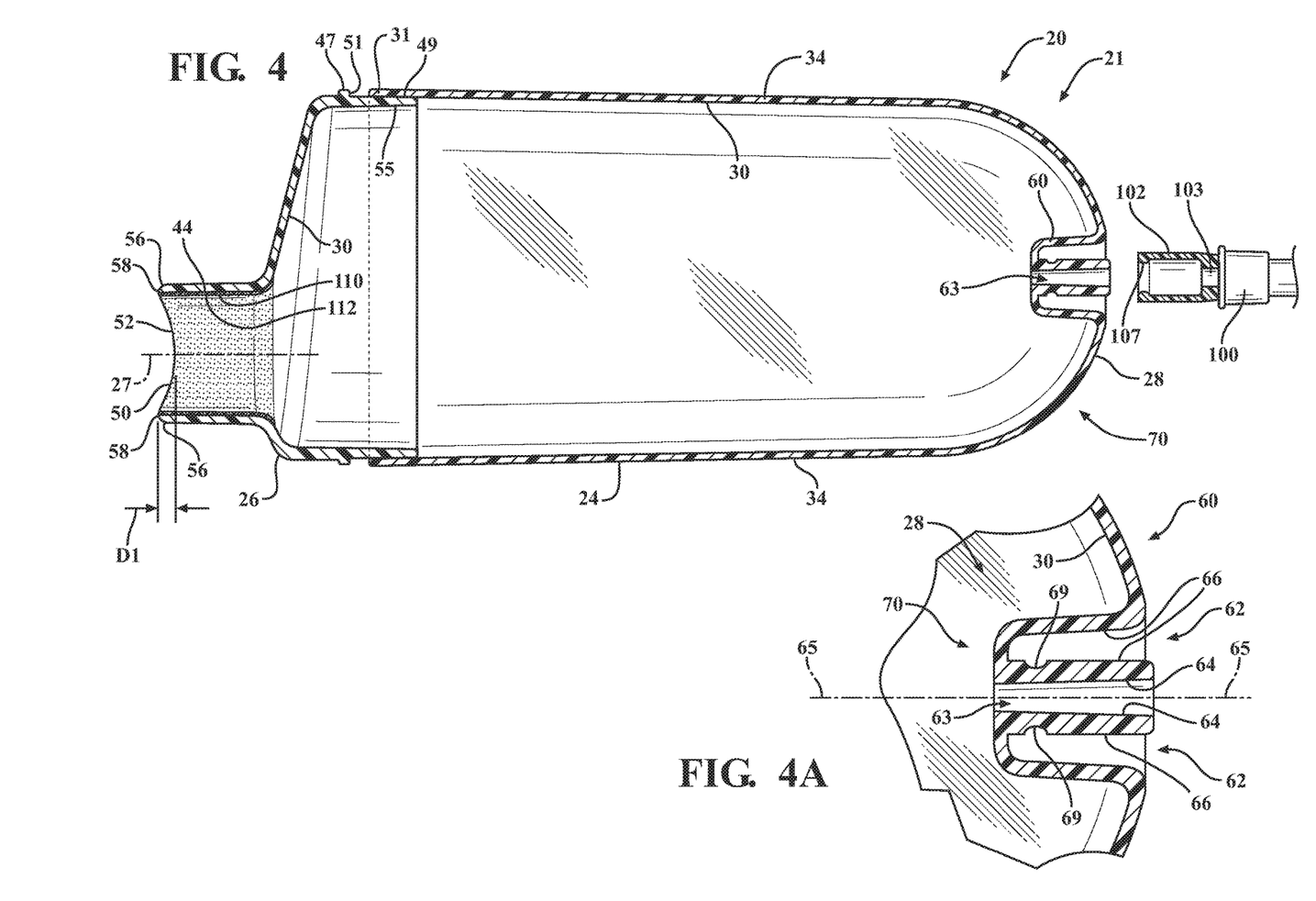
FIG. 4 is a section view of an implant removal system including the implant removal device of FIG. 2 prior to coupling the suction device.
FIG. 4A is a close-up section view of the connector port of FIG. 4.
Figure 5:
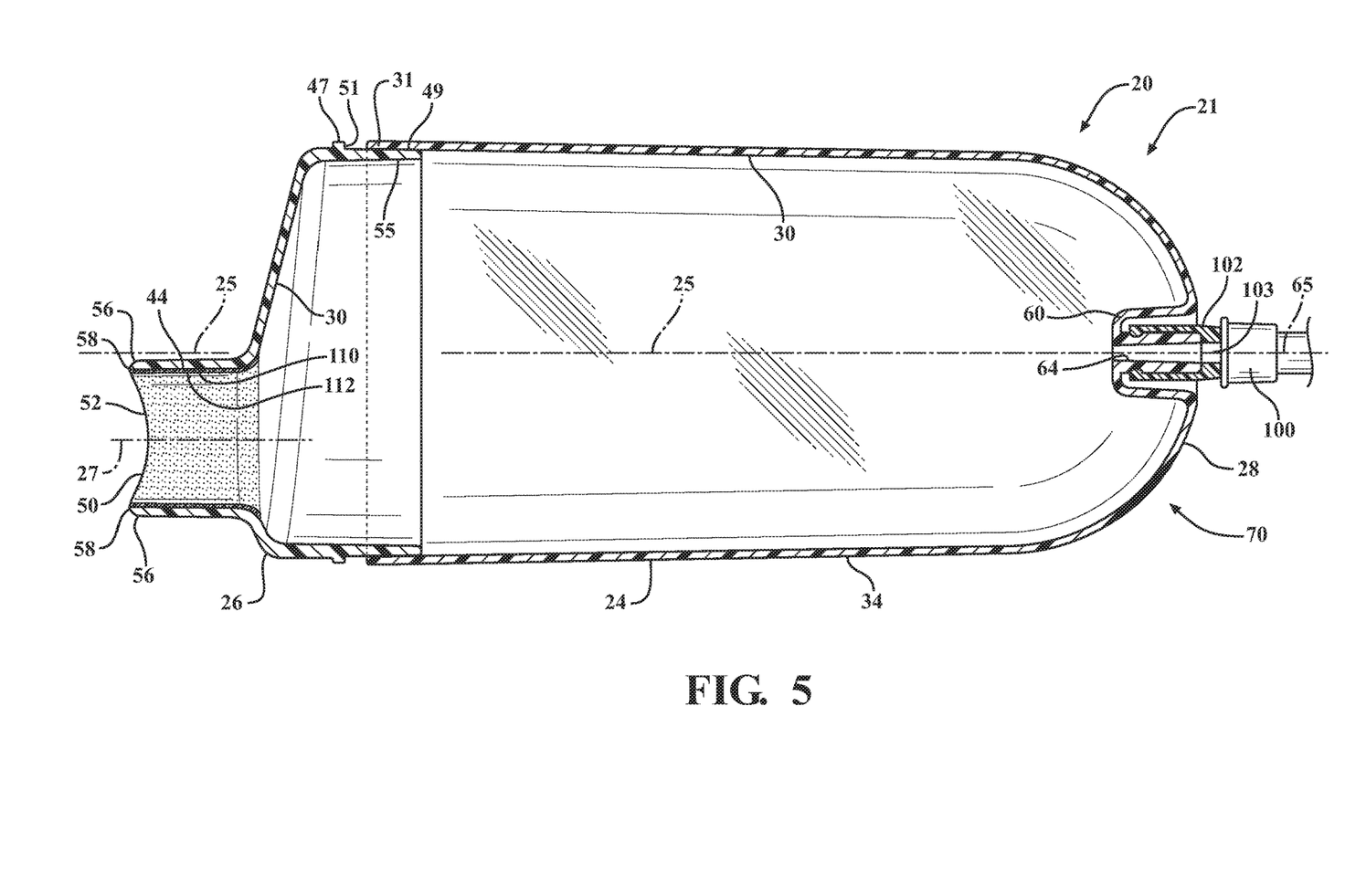
FIG. 5 is a section view of an implant removal system including the implant removal device of FIG. 2 after coupling the suction device.

In certain of these embodiments, as best shown in FIGS. 1A, 4 and 5, the outer peripheral end 42 of the first cap 29 includes a ledge 45 extending transverse from a shoulder 47. The ledge 45 and shoulder 47 are shaped such that the outer surface 49 of the ledge 45 is press fit against the interior container surface 30 of the terminal end region 31 of the middle portion 24 and wherein the inward surface 51 of the shoulder 47 is adjacent to the outer terminal surface 33 of the middle portion 24.

In certain alternative embodiments (not shown), as opposed to press fitting the ledge 45 of the first cap 29 to the interior container surface 30 of the middle portion 24, the exterior container surface 34 of the middle portion 24 may be press fit to an inner surface 51 of the ledge 45 of the first cap 29, with the inward surface 51 of the shoulder 47 still being adjacent to the outer terminal surface 33 (but wherein the shoulder 47 extends inwardly instead of outwardly. In certain related embodiments, in order to permanently secure the first cap 29 to the middle portion 24 in these alternative embodiments, an ultrasonic welding process may be performed, or an adhesive may be included, between the outer surface 49 and interior container surface 30 (or in the alternative arrangement between the inner surface 51 and the exterior container surface 34), and/or between the inward surface 51 and the outer terminal surface 33 to secure or otherwise affix the first cap 29 to the middle portion 24 if desired.

Figure 1B:
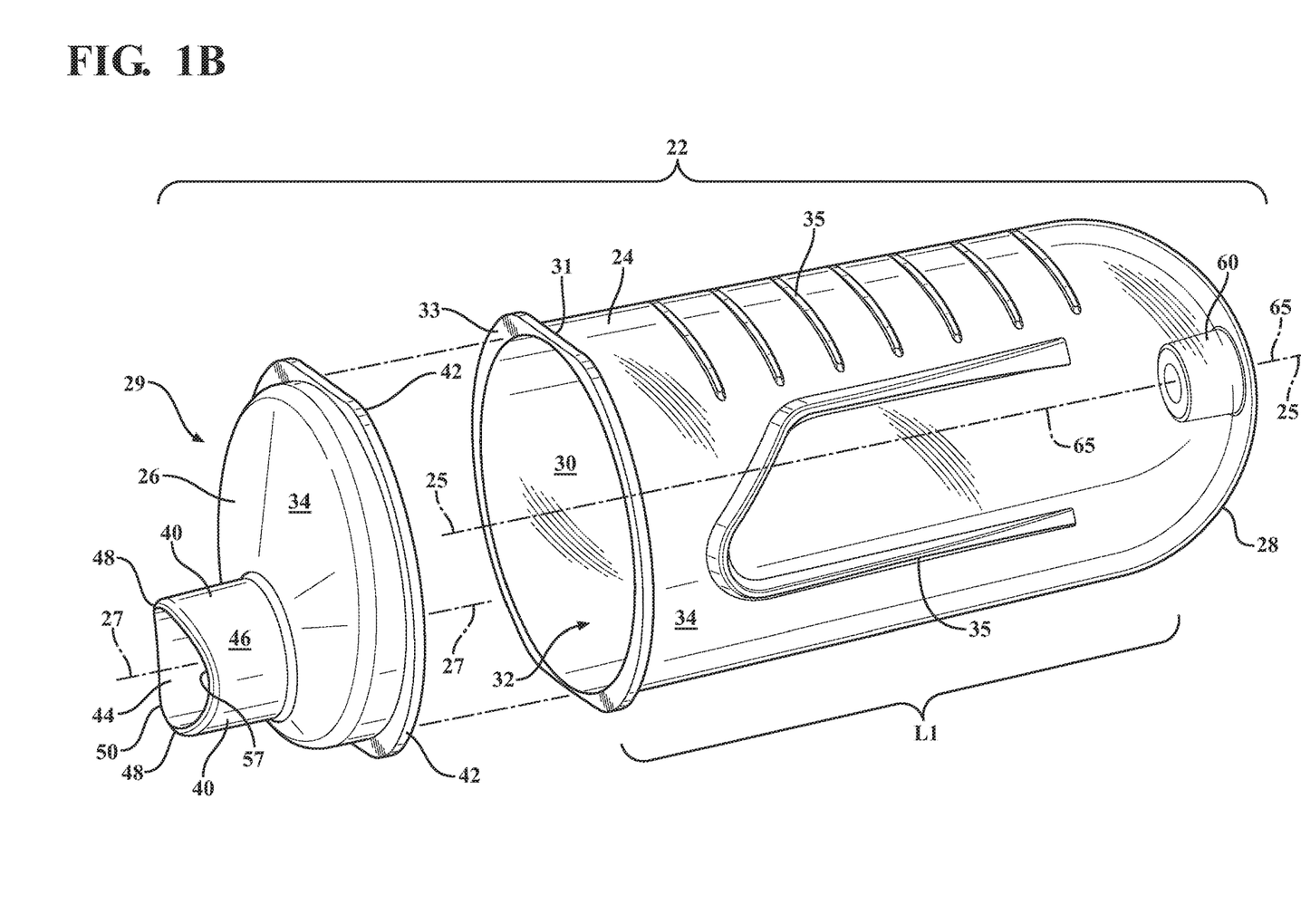
FIG. 1B is a perspective view of the first end of the implant removal device according to another exemplary embodiment.
Figures 2, 3:
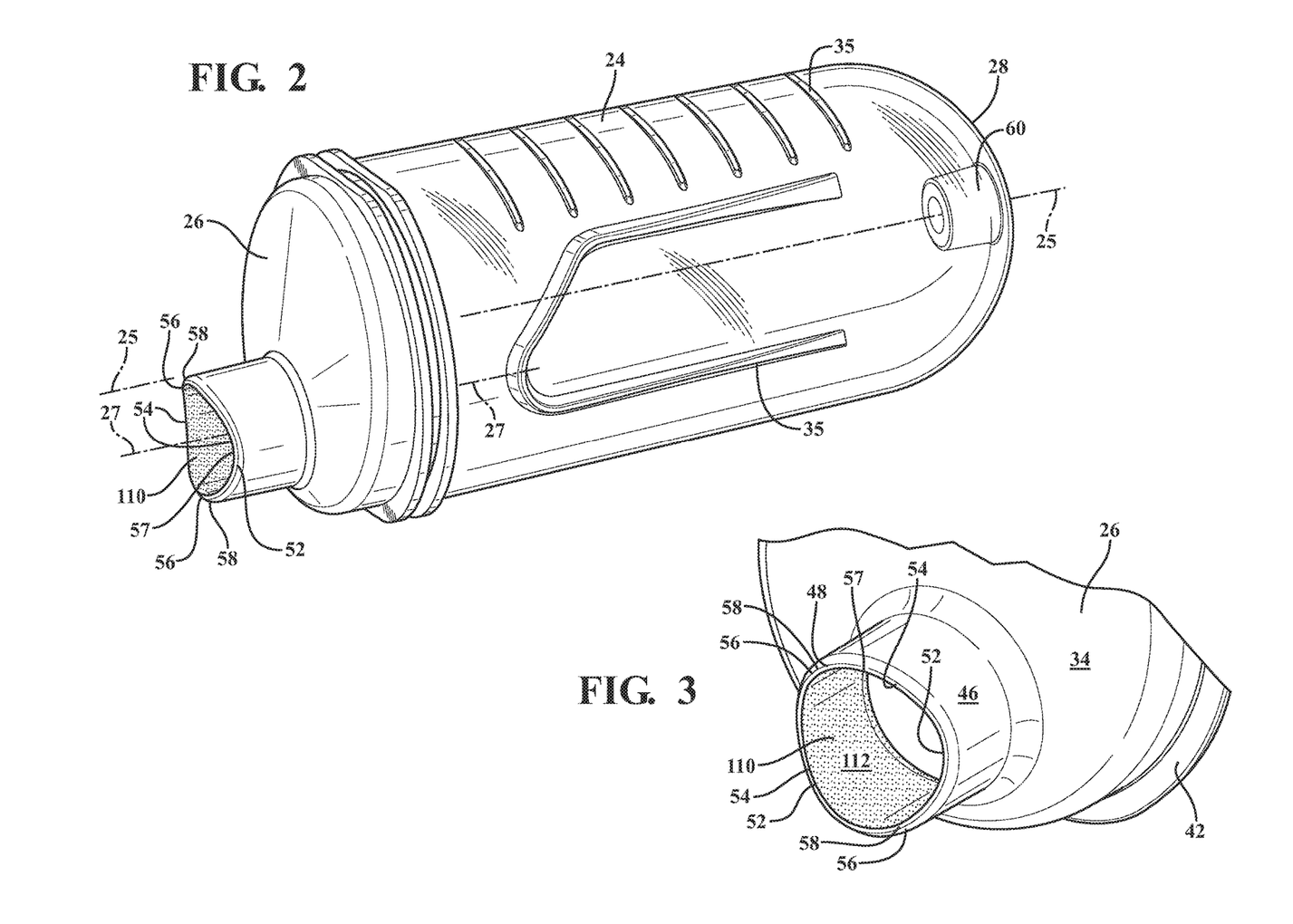
FIG. 2 is a perspective view of the implant removal device of FIG. 1A wherein the first end is coupled to the middle portion of the hollow container.
FIG. 3 is a close-up perspective view of the nozzle of FIG. 2.

In another alternative embodiment of the first cap 29 as shown in FIG. 1B, as opposed to a press fitting the outer peripheral end 42 of the first cap 29 to the middle portion 24, an inward terminal surface 55 of the outer peripheral end 42 of the first cap 29 may simply be abutted to the outer terminal surface 33 of the outer terminal region 31 of the middle portion 24 and be secured thereto via ultrasonic welding or through the use of an adhesive.

In certain embodiments, a connector port 60 is coupled to the second end 28 of the hollow container 22. The connector port 60, as best shown in FIG. 4A, includes a connector receiving region 62 that is adapted for connection to the suction device 100. In particular, as further shown in FIG. 5, the connector interior region 62 is adapted to receive an external portion 102 of the suction device 100.

In certain embodiments, the connector interior region 62 has an internal opening 63 that is open to, and forms a portion of, the volume 32 of the hollow container 22. The internal opening 63 of the connector interior region 62 is also open with an internal opening 103 of the suction device 100 when the suction device 100 is coupled to the connector port 60, with the internal opening 103 defined within the external portion 102. As such, when negative pressure is actuated from the suction device 100, suction is created (shown as arrow 200 in FIG. 6) through the internal opening 103, the internal opening 63, and into the volume 32 of the hollow container 22 that is then used that draw the implant 80 (including the shell 82 and gel 84) through the nozzle opening 50 and into the volume 32.

In certain embodiments, such as shown in FIGS. 4 and 4A, the connector port 60 is integrally formed with the second end 28. In these embodiments, the inner surface 64 of the connector receiving region 62, which defines the internal opening 63, extends outwardly from, or otherwise transitions outwardly from the interior container surface 30 of the second end 28 in an opposite direction from the middle portion 24 relative to the nozzle 40. Similarly, the connector receiving region 62 includes an outer surface 66 that extends outwardly from, or otherwise transitions outwardly away from the exterior container surface 34 of the first end 26. The outer surface 66 also includes a depressed region 69 that receives a corresponding flange 107 of the external portion 102 of the suction device 100 to secure the suction device 100 to the connector portion 60.

The connector port 60 also defines a connector axis 65. In particular, the connector axis 65 is defined within the internal opening 63 and is generally aligned parallel to the length of the inner surface 64 of the connector port 60.

In certain embodiments, such as shown in the Figures, the connector axis 65 is parallel to the nozzle axis 27. In further embodiments, the connector axis 65 is offset from the longitudinal axis 25. Still further, in certain embodiments, the connector axis 65 is offset from the longitudinal axis 25 and is radially spaced from the nozzle axis 27 relative to the longitudinal axis 25.

In still further embodiments, the connector port 60 is coupled to the second end 28 and extends in a direction transverse to the longitudinal axis 25. In certain of these embodiments, the connector port 60 is coupled to the second end 28 and extends in a direction normal to the longitudinal axis 25.

In still further embodiments, as opposed to being coupled to the second end 28, the connector port 60 is coupled to the middle portion 24 and extends in a direction transverse to the longitudinal axis 25. In certain of these embodiments, the connector port 60 is coupled to the middle portion 24 and extends in a direction normal to the longitudinal axis 25.

In certain other embodiments, the connector port 60 is a separate structure that is coupled to the second end 28. In certain of these embodiments, the outer surface 66 of the connector port 60 is coupled to the interior container surface 30 of the second end 28, while in further alternative embodiments the inner surface 64 of the connector port 60 is coupled around the exterior container surface 34 of the second end 28. In either of these embodiments, ultrasonic welding or an adhesive material may be introduced between the connector port 60 and the second end 28 to secure the connector port 60 to the first end 28. In embodiments wherein the connector port 60 is coupled to the middle portion 24 and is a separate structure from the middle portion 24, a similar kind of coupling and securing via ultrasonic welding or through an adhesive can occur.

In certain embodiments, the hollow container 22 includes a second cap 70 defining the second end 28. In these embodiments, the second cap 70 is integrally formed with the middle portion 24 as a one-piece structure, such as best shown in FIGS. 4 and 5.

Alternatively, the second cap 70 may be coupled to another terminal end surface (not shown) of the middle portion 24 in a manner similar to the connection of the first cap 29 to the terminal end region 31 of the middle portion 24 as described above.

The hollow container 22, in certain embodiments, is formed from a material having physical properties, particularly in terms of leakage prevention, durability and strength, appropriate for the temporary acceptance of the shell 82, any silicone gel 84, and associated medical waste from the patient 95. Preferably, the hollow container 22 is transparent such that a doctor can confirm the acceptance of the breast implant shell 82, any silicone gel 84, and associated medical waste from the patient 95 during the surgical procedure. In certain embodiments, however, the separate first end 26 (including the nozzle 40) may be formed from an opaque material, such as an opaque plastic material. Still further, as noted above, the material used in the nozzle 40 should have sufficient rigidity to maintain its shape when pressed against the shell 82 of the implant 80 during the removal process. Yet still further, it is desirable that the material used in forming the hollow container 22 has sufficient rigidity and strength to withstand collapsing upon the introduction of negative pressure, in the range of 150-500 mm Hg (mercury), during the removal process. Even still further, it is desirable that such material retain their physical properties, including transparency, after a sterilization process such as through e-beam sterilization.

Exemplary materials for forming the hollow container 22, or any component thereof (such as the nozzle 40), include, but are not limited, thermoplastic materials such as polycarbonate. In certain embodiments, the materials for each separate piece of the hollow container 22 are formed from the same exemplary material, while in other embodiments the separate pieces may be formed of different materials, or slightly different formulations of the same general thermoplastic material. For example, in embodiments, wherein the first end 26 is formed from an opaque material, while the middle portion 24 and second end 28 are formed from a transparent material, the difference in such materials could simply occur by adjusting the formulations to include additives (such as including a fillers or pigments in the first end 26 that are not present, or present in differing amounts, in the middle portion 24 or second end 28). Alternatively, the polymer composition of the thermoplastic materials may be different (such as through the use of a polycarbonate material in one instance and a polyurethane in another instance, or alternatively wherein the generally polycarbonate material is modified in some other manner (such as through changes in number average molecular weights or by modifying the structure to include additional chemical groups). Other materials, such as thermosetting polymeric materials or glass, may also form one or more of the separate components of the hollow container 22.

In certain embodiments, a coating layer 110 is applied to the interior nozzle surface 44 of the nozzle 40. The coating layer 110 is in the form of a low friction coating layer 110 formed from a low friction material, in which the outer surface 112 (shown in FIG. 5) of the coating layer 110, opposite the interior nozzle surface 44, has lower surface friction than the corresponding surface friction of the interior nozzle surface 44. In certain embodiments, in addition to forming a low surface friction outer surface, the coating material also is a hydrophilic coating, which is believed to provide the outer surface layer with an increased amount of lubricity.

The lower surface friction properties of the outer surface 112 of the coating layer 110, alone or in combination with the increase in hydrophilicity, aids in preventing the implant 80 and any associated residual medical waste (such as blood, tissue, water etc.) from a patient from adhering onto the outer surface 112 during use of implant removal device 21 in removing the implant 80 as compared with an uncoated interior nozzle surface 44, thereby increasing the efficiency of the implant removal process.

In still further embodiments, in addition to having the lower surface friction properties, the outer surface 112 of the coating layer 110 may also provide increased durability properties, or enhanced durability properties, as compared with devices 21 not include such a coating layer 110. Further, the coating layers 110 provided have sufficient bonding strength to the interior nozzle surface 44 such that they are not removed, delaminated, or otherwise degrade during the implant removal process.

Exemplary, non-limiting coating compositions used to form the coating layer 110 include low friction, hydrophilic coating compositions sold under the tradename Serene™, commercially available from Surmodics, Inc. of Eden Prairie, Minn. and hydrophobic coating compositions sold under the tradename Hydak®, commercially available from Biocoat, Inc., of Horsham, Pa. However, other coating compositions for forming layers 110 having specific properties or combination of properties are also contemplated.

In even further embodiments, a flexible diaphragm may be provided that is positioned at the interface between the hollow container 22 and the suction device 100, or within the interior of the hollow container 22 at a position near, along or adjacent to the connector port 60, to separate the volume 32 of the hollow container 25 from the suction device 100. The flexible diaphragm functions to limit contamination of the suction device 100 from the removed implant 80 during use, the flexible diaphragm also prevents the introduction of cross contamination into the volume 32 of the hollow container 22, and into the patient 95 via the volume 32 of the hollow container 22, from the outside environment. When included, the flexible diaphragm does not adversely impact the generation of negative pressure from the suction device 100 within the volume 32 of the hollow container 22.

The present invention also is directed to an implant removal system 20, including the afore-mentioned implant removal device 21, and an associated method which is used in a surgical procedure to remove a ruptured silicone breast implant 80 from a patient 95. In the implant removal system 20, as shown in FIG. 6, the implant removal device 21 is coupled to a suction device 100, such as a wall suction device 100 coupled to and extending from a wall 140 within an operating room 150 which when actuated provides negative pressure, in the range of 150-500 mm Hg, within the volume 32 of the hollow container 22 and through the nozzle opening 50 sufficient to facilitate the removal of the shell 82 and silicone gel 84 from the patient 95.

The suction device 100 is conventional in nature and is of the type found in hospital or medical settings to provide a vacuum source for surgical procedures. The suction device 100 may be mounted in an operating room 150 of a medical facility, or alternatively may be mobile.

In particular, as best shown in FIG. 6, during the surgical procedure for removal on an implant, here shown as a ruptured silicone breast implant 80, a small incision 90 is made in the skin of a patient 95 in order to access the ruptured implant 80.

The device 21, which has been sterilized before use such as through e-beam sterilization as described above, is then brought into proximity with the incision 90 and is utilized to remove the implant 80. More particularly, the device 21 is positioned on the surface of the skin near the incision 90 between the ends of the incision 90, with the nozzle opening 50 positioned in closest proximity to the skin of the patient 95 for easier insertion. The nozzle 40 is then inserted within the small incision 90 in the skin and brought into proximity to the implant 80. The size of the small incision 90 is preferably roughly equal to the cross-sectional width of the nozzle 40 such that the nozzle 40 is surrounded by the tissue and skin of the patient 95 after insertion, although the size could be larger if desired based on the preference of the doctor.

Preferably, during the insertion process, the gripping portions 156 are brought into pressing contact with the shell 82 of the implant 80. As noted above, the rigidity of the nozzle 40 and the gripping portions 156 allows the device 21 to maintain its internal position within the incision 90 of the patient 20 during the implant removal process.

The suction device 100 is coupled to the connector port 60 either prior to the insertion of the nozzle 40 or after the insertion of the nozzle 40. Typically this is accomplished by inserting the external portion 102 of the suction device 100 into the connector receiving portion 62 and securing the flange 107 into the depressed portion 107 of the outer surface 66. The suction device 100 is then actuated, thereby creating negative pressure (i.e., vacuum suction) within the volume 32 of the hollow container 22 (shown by arrow 200 in FIG. 6) sufficient to draw out the breast implant shell 82 and cohesive silicone gel 84 through the nozzle opening 50 of the device 21 and into the volume 32 of the hollow container 22. As illustrated in FIG. 6, a portion of the silicone gel 84 has been removed to the volume 32, while the majority of the gel 84 contained in the shell 82 still remains in the patient 95, such as immediately after actuation. As noted above, in certain embodiments, such negative pressure may be between 150 and 500 mm Hg. If needed, the negative pressure of the suction device 100 may be increased or decreased relative to the desired range. Because the middle portion 24 of the device 21 is transparent, the doctor can observe and confirm the introduction of the shell 82 and silicone gel 84 in the volume 32 of the hollow container 22 during the removal process as the negative pressure is actuated.

Upon confirmation, typically visual confirmation by the doctor, that a desired amount of the implant shell 82 and silicone gel 84 has been removed from the patient 95 and is visible through the transparent middle portion 24 in the volume 32, the suction device 100 is turned off, and the device 21 is removed from the incision 90, as shown in FIG. 7. The suction device 100 is then disconnected from the connector port 60. Any residual silicone gel 84 or shell 82 of the implant 80 that was not removed by the device 21 can then be removed from the patient through the use of surgical sponges or other known manual extraction surgical techniques.

The device 21, including the extravagated silicone gel 84 and shell 82 contained within the volume 32 of the hollow container 22 as best illustrated in FIG. 7, may be disposed of as medical waste. Alternatively, such materials may be removed from the device 21, and the device 21 can be cleaned, sterilized, and reused as desired.

The claimed invention differs from what currently exists. There is no implant removal device 21 available which is able to be sterilized prior to use and will assist in removal of an implant 80 (or the shell or gel), such as a ruptured breast implant, as is described herein. This invention is an improvement on what currently exists. The device removes the vast majority of the extravagated silicone and the shell and traps it into an easily disposed unit which substantially expedites the process as well as limits contamination.

While the device 21 is ideally suited for the removal of silicone breast implants, and in particular ruptured silicone breast implants, the device 21 is also appropriate for use, in the method described above, for removal of other types of implants having a shell and material contained within a shell (such as silicone gel, saline, or some other filling material).

The invention has been described in an illustrative manner, and it is to be understood that the terminology which has been used is intended to be in the nature of words of description rather than of limitation. Many modifications and variations of the present invention are possible in light of the above teachings, and the invention may be practiced otherwise than as specifically described.

What is claimed is:

1. A removal device for removing an implant, said removal device comprising:
    a hollow container extending between a first end and second end along a longitudinal axis with a middle portion disposed between said first and second ends, and said hollow container having an interior container surface defining a volume for receiving and containing the implant, wherein said hollow container is formed from a material having sufficient rigidity to not collapse under normal operating pressures between 150-500 mm Hg:
    a connector port coupled to said second end of said hollow container, and adapted for connection to a suction device; and a nozzle, having a cylindrical body, coupled to said first end of said hollow container, said nozzle extending away from said first end along a nozzle axis with said nozzle having an interior nozzle surface and terminating at a nozzle opening, wherein said nozzle axis is offset from said longitudinal axis of the hollow container, said nozzle opening comprising:
- a plurality of gripping portions and a plurality of recessed portions for engaging the implant with said nozzle, said nozzle configured to receive the implant through said nozzle opening and into said hollow container,
- wherein each of said plurality of gripping portions define a terminal end surface having an apex,
- wherein each of said plurality of recessed portions is curved and has a vertex,
- wherein said apex of a respective gripping portion is spaced further from said first end of said hollow container than said vertex of a respective recessed portion, with a distance between said apex of said respective gripping portion and said vertex of said respective recessed portion defining a depth of said respective recessed portion, and
- wherein one of the said plurality of gripping portions is aligned proximate the longitudinal axis of the hollow container.

2. The removal device of claim 1, wherein said nozzle is formed from a material having sufficient rigidity such that said nozzle resists deformation and said nozzle opening remains open for permitting passage of the implant into said hollow container to occupy the volume.

3. The removal device of claim 1, wherein said hollow container includes a first cap defining said first end with an outer peripheral end of said first cap being one of press fit or ultrasonically welded to said middle portion.

4. The removal device of claim 1, wherein said hollow container includes a second cap defining said second end with said middle portion integrally formed with said second cap.

5. The removal device of claim 1 further comprising a low friction coating material bonded to said interior nozzle surface to form a coating layer, wherein an outer surface of said coating layer has lower surface friction than said interior nozzle surface.

6. The removal device of claim 1, wherein an exterior surface of said hollow container includes one or more recesses or protrusions for gripping said exterior surface of said hollow container.

7. The removal device of claim 1, wherein said hollow container is transparent.

8. The removal device of claim 1, wherein one or both of said nozzle and said hollow container are formed from a polycarbonate material.

9. A removal device for removing an implant, said removal device comprising:
- a hollow container extending between a first end and a second end along a longitudinal axis with a middle portion disposed between said first and second ends, and said hollow container having an interior container surface defining a volume for receiving and containing the implant, wherein said hollow container is formed from a material having sufficient rigidity to not collapse under normal operating pressures between 150-500 mm Hg;
- a connector port coupled to said second end of said hollow container, and adapted for connection to a suction device, and
- a nozzle, having a cylindrical body, coupled to said first end of said hollow container extending away from said first end along a nozzle axis with said nozzle having an interior nozzle surface and terminating at a nozzle opening, and said nozzle axis being offset from said longitudinal axis such that said nozzle opening is offset from said middle portion of said hollow container along said longitudinal axis for aligning with the implant during a removal process,
- wherein said nozzle opening of said nozzle includes at least one gripping portion and at least one recessed portion, wherein said at least one gripping portion is aligned with said longitudinal axis, and
- wherein said nozzle opening is configured to engage the implant with said nozzle configured to receive the implant through said nozzle opening and into said hollow container.

10. The removal device of claim 9, wherein said connector port defines a connector axis parallel to said longitudinal axis.

11. The removal device of claim 10, wherein said connector axis and said nozzle axis are radially spaced from each other relative to said longitudinal axis.

12. The removal device of claim 9, wherein said connector port defines a connector axis parallel to said longitudinal axis and said nozzle axis such that said nozzle extends in an opposite direction from said connector port.

13. The removal device of claim 9, wherein said at least one gripping portion comprises a plurality of gripping portions, and wherein said at least one recessed portion comprises a plurality of recessed portions, and wherein a respective one of said plurality of recessed portions is curved between each respective pair of said plurality of gripping portions.

* * * * *